United States Patent
Kanamoto et al.

(10) Patent No.: US 9,534,633 B2
(45) Date of Patent: Jan. 3, 2017

(54) DOUBLE-ROW ROLLING BEARING

(71) Applicants: Takahiro Kanamoto, Mie (JP); Wakana Inoue, Mie (JP)

(72) Inventors: Takahiro Kanamoto, Mie (JP); Wakana Inoue, Mie (JP)

(73) Assignee: NTN CORPORATION, Osaka (JP)

( * ) Notice: Subject to any disclaimer, the term of this patent is extended or adjusted under 35 U.S.C. 154(b) by 0 days.

(21) Appl. No.: 14/436,210

(22) PCT Filed: Oct. 8, 2013

(86) PCT No.: PCT/JP2013/077355
§ 371 (c)(1),
(2) Date: Apr. 16, 2015

(87) PCT Pub. No.: WO2014/069185
PCT Pub. Date: May 8, 2014

(65) Prior Publication Data
US 2015/0285308 A1    Oct. 8, 2015

(30) Foreign Application Priority Data
Nov. 5, 2012 (JP) ................................. 2012-243713

(51) Int. Cl.
F16C 33/60    (2006.01)
F16C 19/18    (2006.01)
(Continued)

(52) U.S. Cl.
CPC ............. F16C 33/605 (2013.01); F16C 19/08 (2013.01); F16C 19/184 (2013.01); F16C 33/60 (2013.01);
(Continued)

(58) Field of Classification Search
CPC ....... F16C 19/542; F16C 19/543; F16C 33/58; F16C 33/60; F16C 33/605
See application file for complete search history.

(56) References Cited

U.S. PATENT DOCUMENTS 4,138,169 A * 2/1979 Stolz .................. B60B 27/0005
                                                              384/510
4,425,009 A * 1/1984 Fillon .................. F16C 19/184
                                                              29/898.062
(Continued)

FOREIGN PATENT DOCUMENTS

CN    201231644    5/2009
CN    201982254    9/2011
(Continued)

OTHER PUBLICATIONS

International Search Report issued Jan. 14, 2014 in International (PCT) Application No. PCT/JP2013/077355.
(Continued)

Primary Examiner — Thomas R. Hannon
(74) Attorney, Agent, or Firm — Wenderoth, Lind & Ponack, L.L.P.

(57) ABSTRACT

A double-row rolling bearing includes an outer member having two raceway surfaces on an inner circumference thereof, an inner member having two raceway surfaces on an outer circumference thereof, the inner member being arranged on an inner side of the outer member, two rows of rolling elements assembled into a space between each of the two raceway surfaces of the outer member and each of the two raceway surfaces of the inner member, and a retainer for retaining the rolling elements. Any one of the outer member and the inner member includes a pair of raceway rings, both of the pair of raceway rings being fastened with a fixing bolt and having positioning holes into which a positioning mem-
(Continued)

ber is fit-inserted, to thereby suppress misalignment in a radial direction of the pair of raceway rings.

16 Claims, 9 Drawing Sheets

(51) Int. Cl.
 *F16C 19/08* (2006.01)
 *F16C 33/78* (2006.01)
 *F16C 25/06* (2006.01)
(52) U.S. Cl.
 CPC .............. *F16C 25/06* (2013.01); *F16C 33/785* (2013.01); *F16C 2226/62* (2013.01)

(56) References Cited

U.S. PATENT DOCUMENTS

| | | | |
|---|---|---|---|
| 4,730,946 A | 3/1988 | Cain | |
| 6,269,711 B1 * | 8/2001 | Tejima | F16H 49/001 384/512 |
| 6,406,188 B1 * | 6/2002 | Lin | F16C 19/183 384/504 |
| 7,931,409 B2 * | 4/2011 | Kobayashi | B60B 27/0005 301/105.1 |
| 9,057,406 B2 * | 6/2015 | Hofmann | F16C 19/386 |
| 2009/0131235 A1 * | 5/2009 | Katsuno | F16C 19/505 483/18 |

FOREIGN PATENT DOCUMENTS

| | | |
|---|---|---|
| CN | 102364135 | 2/2012 |
| CN | 202790079 | 3/2013 |
| JP | 2-87118 | 7/1990 |
| JP | 2001-56024 | 2/2001 |
| JP | 2001-59518 | 3/2001 |
| JP | 2006-144829 | 6/2006 |
| JP | 2006-266458 | 10/2006 |

OTHER PUBLICATIONS

International Preliminary Report on Patentability and Written Opinion of the International Searching Authority issued May 5, 2015 in International (PCT) Application No. PCT/JP2013/077355.
Extended European Search Report issued Jun. 29, 2016 in corresponding European Application No. 13850667.0.
Office Action issued Jun. 23, 2016 in corresponding Japanese Application No. 2012-243713, with English translation.
Office Action issued Sep. 1, 2016 in corresponding Chinese Application No. 201380057465.4, with partial English translation.

* cited by examiner

DOUBLE-ROW ROLLING BEARING

TECHNICAL FIELD

The present invention relates to a double-row rolling bearing to be used in various fields including industrial machinery, and more particularly, to an ultrathin double-row rolling bearing to be used in medical equipment including a CT scanner.

BACKGROUND ART

FIG. 5 illustrates an example of a CT scanner 100 as one type of medical equipment. The CT scanner 100 diagnoses and analyzes a pathological symptom through irradiation with an X-ray or the like. The CT scanner 100 includes an examination unit 101 having an opening 101A, and a bed unit 102 movable in the opening 101A of the examination unit 101 with an examinee 110 such as a human body lying thereon. The examination unit 101 includes a ring-shaped rotator 105 (gantry) having an X-ray irradiation device 103 and a detection unit 104 arranged so as to be opposed to each other in a diameter direction. The rotator 105 is rotatably supported by a cylindrical stationary unit 106 through intermediation of a bearing 51.

The CT scanner 100 rotates the rotator 105 about the bed unit 102 while irradiating the examinee 110 with an X-ray from the X-ray irradiation device 103 so as to detect the X-ray having passed through the examinee 110 with the detection unit 104, thereby obtaining a tomographic image of the examinee 110.

In the CT scanner 100, in order to form the opening 101A of the examination unit 101 into such a dimension that the examinee 110 may pass through the opening 101A (diameter of about 1 m), and to downsize the CT scanner 100 itself, it is necessary to reduce a space of a rotation support unit 107 having the bearing 51 arranged therein. Therefore, a so-called ultrathin double-row rolling bearing having a significantly small ball diameter with respect to a pitch circle diameter of balls is used as the bearing 51. In this case, the ultrathin rolling bearing refers to an ultrathin large-scale rolling bearing having an inner diameter of 650 mm or more and having a value of a ratio Db/PCD of a diameter Db of each of rolling elements to a pitch circle diameter PCD of the rolling elements of 0.03 or less.

Patent Document 1 discloses such an ultrathin double-row rolling bearing that an inner member is formed of a pair of raceway rings, which are fastened with a fitting structure while a concentric state is kept. FIG. 9 illustrates this double-row rolling bearing. The double-row rolling bearing 51 mainly includes an outer member 52, an inner member 53, rolling elements 54, and retainers 55. The double-row rolling bearing is a double-row angular ball contact bearing having balls 54 arranged in two rows as the rolling elements. The balls 54 and 54 assembled into a space between each of two rows of raceway surfaces 56 and 56 of the outer member 52 and each of two rows of raceway surfaces 57 and 57 of the inner member 53 are brought into contact with the raceway surfaces 56 and 57 at a contact angle, and the double-row angular ball contact bearing is constructed in back-to-back arrangement so as to be suitable for supporting a moment load.

The inner member 53 is formed of a pair of raceway rings 53a and 53b. The raceway ring 53a has a screw hole 58a, and the raceway ring 53b has a fit-insertion hole 58b. The raceway rings 53a and 53b are fastened with a bolt 59. In this case, due to the fitting structure formed by a projection 60a formed on the raceway ring 53a and a recess 60b formed on the raceway ring 53b, misalignment between the raceway rings 53a and 53b is prevented. The bolt 59 is fastened to pressurize the raceway ring 53b toward the raceway ring 53a side, thereby applying a preload (minus clearance) to the inside of the bearing.

PRIOR ART DOCUMENTS

Patent Documents

Patent Document 1: JP 2006-266458 A

SUMMARY OF THE INVENTION

Problems to be Solved by the Invention

However, it has been found that the fitting structure of the double-row rolling bearing 51 disclosed in Patent Literature 1 has the following problems. That is, in the fitting structure formed by the projection 60a formed on the raceway ring 53a and the recess 60b formed on the raceway ring 53b, it is necessary to process the projection 60a and the recess 60b to a minute fitting clearance with high accuracy. However, the projection 60a and the recess 60b are formed on the thin raceway rings 53a and 53b each having a large diameter, thereby being difficult to process the projection 60a and the recess 60b with high accuracy. Further, there is a problem in that, when an attempt is made to process the projection 60a and the recess 60b with high accuracy, a manufacturing cost significantly increases.

On the other hand, it has also been found that, when an allowable dimension range of the fitting clearance of the projection 60a and the recess 60b is mitigated so as to reduce the manufacturing cost, the following problem arises. For example, in the CT scanner 100 illustrated in FIG. 5, as described above, the examination unit 101 includes the ring-shaped rotator 105 (gantry) having the X-ray irradiation device 103 and the detection unit 104 arranged so as to be opposed to each other in the diameter direction. The rotator 105 is rotatably supported by the cylindrical stationary unit 106 through intermediation of the bearing 51 in a state close to a cantilever. Therefore, the bearing 51 is in a severe use environment in which a large moment load is applied to the bearing 51 and the bearing 51 rotates at a high speed of 120 rpm or more in such a load state.

Further, in medical equipment, consideration is required so that a patient who is to undergo an examination does not feel anxiety or fear. In particular, in the case of the CT scanner, the patient himself/herself enters through a region like an entrance of a tunnel called a gantry, and hence a mechanical operation noise and an electrical excitation noise are not favorable. As a result, the bearing capable of achieving low noise, low vibration, and high rigidity is required. Further, excellent durability is desired in the CT scanner because the CT scanner is expensive medical equipment, and hence the bearing having long life is required.

Due to the above-mentioned bearing use state, when the allowable dimension range of the fitting clearance of the projection 60a and the recess 60b is enlarged, the misalignment between the pair of raceway rings 53a and 53b cannot be sufficiently suppressed, thereby being difficult to obtain an appropriate preload (minus clearance) in the bearing or a minimum clearance uniformly in the two rows of right and left raceway rings. In particular, at a time of the action of a moment load, there is a concern about a problem such as a preload loss. Thus, it has been found that the bearing has problems in achieving low noise, low vibration, and high rigidity.

In view of the above-mentioned problems, it is an object of the present invention to provide a double-row rolling bearing, which is capable of suppressing misalignment between a pair of raceway rings forming an outer member or an inner member and achieving low noise, low vibration, and high rigidity, and is easily manufacturable at low cost.

Solutions to the Problems

The inventors of the present invention conducted various studies so as to achieve the above-mentioned object, and as a result, achieved the present invention based on a new concept of suppressing misalignment between a pair of raceway rings with a positioning member besides a fixing bolt for the pair of raceway rings.

As a technical measure to achieve the above-mentioned object, according to one embodiment of the present invention, there is provided a double-row rolling bearing, comprising:

an outer member having two raceway surfaces on an inner circumference thereof;

an inner member having two raceway surfaces on an outer circumference thereof, the inner member being arranged on an inner side of the outer member;

two rows of rolling elements assembled into a space between each of the two raceway surfaces of the outer member and each of the two raceway surfaces of the inner member; and a retainer for retaining the rolling elements, any one of the outer member and the inner member comprising a pair of raceway rings, both the pair of raceway rings being fastened with a fixing bolt, the pair of raceway rings having positioning holes into which a positioning member is fit-inserted, to thereby suppress misalignment in a radial direction of the pair of raceway rings.

With the above-mentioned configuration, it is possible to realize the double-row rolling bearing, which is capable of suppressing misalignment in the radial direction between the pair of raceway rings and achieving low noise, low vibration, and high rigidity, and is easily manufacturable at low cost.

With the above-mentioned configuration, end surfaces abutting against each other of the pair of raceway rings have flat surfaces. In this case, the fitting structure can be eliminated. Therefore, manufacturing becomes further easier, and cost can be reduced.

Specifically, it is desired that the pair of raceway rings construct the inner member. In this case, the bearing clearance can be easily set by causing the double-row rolling bearing to be constructed in back-to-back arrangement, which is advantageous to a moment load, and by opposing the end surfaces of the pair of raceway rings to each other.

Commercially available members can be appropriately adopted by using a reamer bolt or a positioning pin as the positioning member, which is preferred in terms of quality and cost.

The number of the positioning holes may be set to two or more. As long as the number of the positioning holes is at least two, the positions in vertical and horizontal directions and in a rotation direction can be determined. In this case, it is preferred that a pitch angle between the positioning holes be set to an angle other than a multiple of a pitch angle between the rolling elements. The reason for this is as follows. After the positioning member is fit-inserted in the positioning hole, the fitting of the positioning member to the positioning hole may become an interference fit. In this case, there is a risk in that strain corresponding to the number of the positioning holes may occur on the raceway surface. This strain may induce and increase a periodic vibration in association with the number of the rolling elements. Therefore, the above-mentioned problem can be solved by setting the pitch angle between the positioning holes to an angle other than a multiple of the pitch angle between the rolling elements.

A relationship of $N \geq W/[\sigma \times (0.6 \sim 0.7) \times A]$ is set to be satisfied, where N represents a number of the reamer bolts, W represents a shear load to be applied, σ represents an allowable tensile stress of the reamer bolt, and A represents a cross-section area of the reamer bolt. Thus, sufficient strength can be ensured with respect to a shear load.

The misalignment between the pair of raceway rings can be effectively suppressed by setting a fitting clearance between the positioning member and each of the positioning holes to be smaller than a fitting clearance between the fixing bolt and a fit-insertion hole for the fixing bolt.

The double-row rolling bearing is constructed in back-to-back arrangement as in the angular ball contact bearing, and thus low noise, low vibration, high rigidity, and high-speed rotation can be achieved. Further, the double-row rolling bearing is preferred to be used in the CT scanner.

Effects of the Invention

According to the one embodiment of the present invention, it is possible to realize the double-row rolling bearing, which is capable of suppressing misalignment between the pair of raceway rings and achieving low noise, low vibration, and high rigidity, and is easily manufacturable at low cost.

EMBODIMENTS OF THE INVENTION

Now, description is made of embodiments of the present invention with reference to the drawings.

A double-row rolling bearing according to a first embodiment of the present invention is described with reference to FIGS. 1 to 5.

Figure 1:
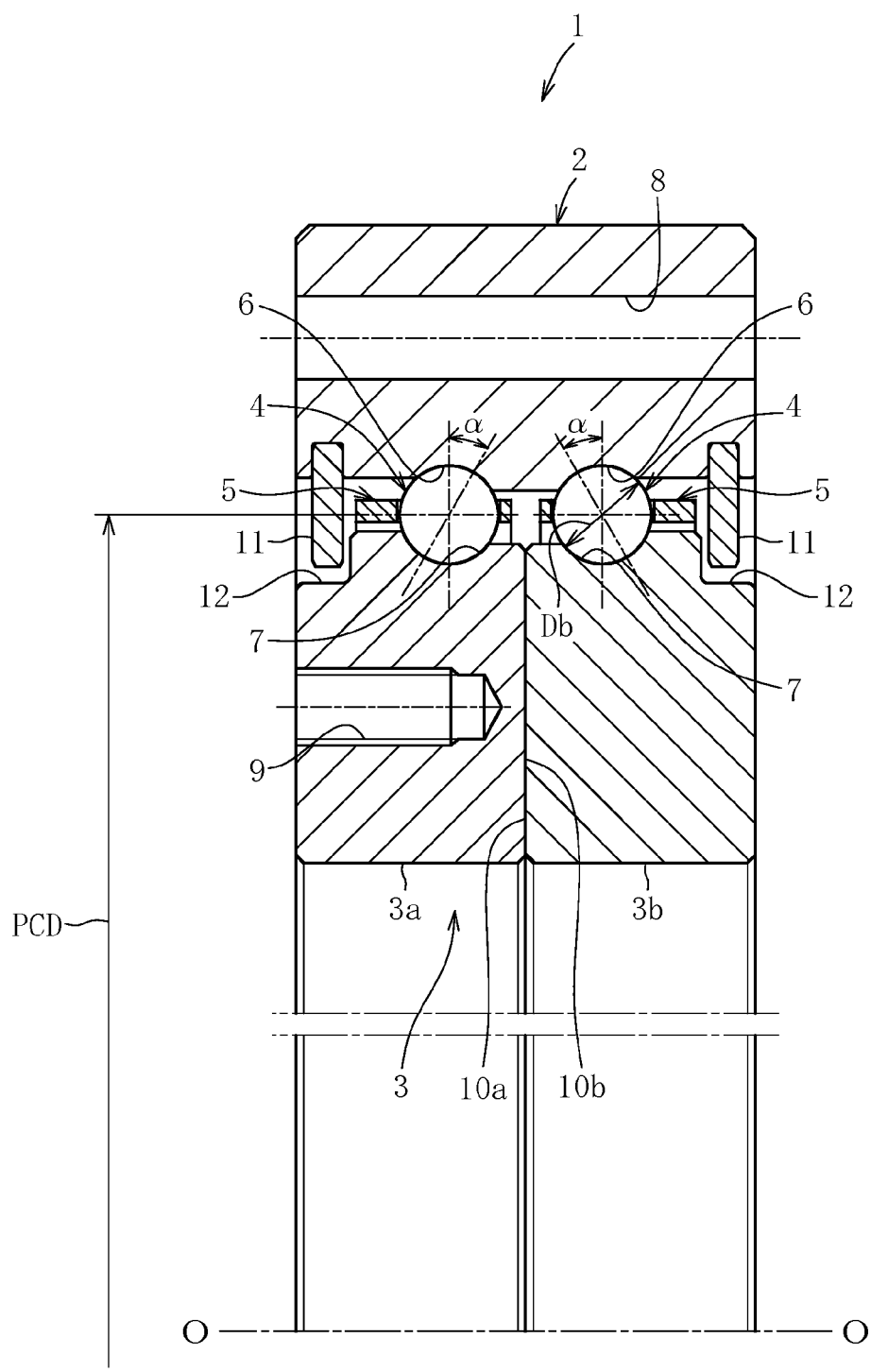
FIG. 1 is a vertical sectional view of a double-row rolling bearing according to a first embodiment of the present invention.
Figure 2:
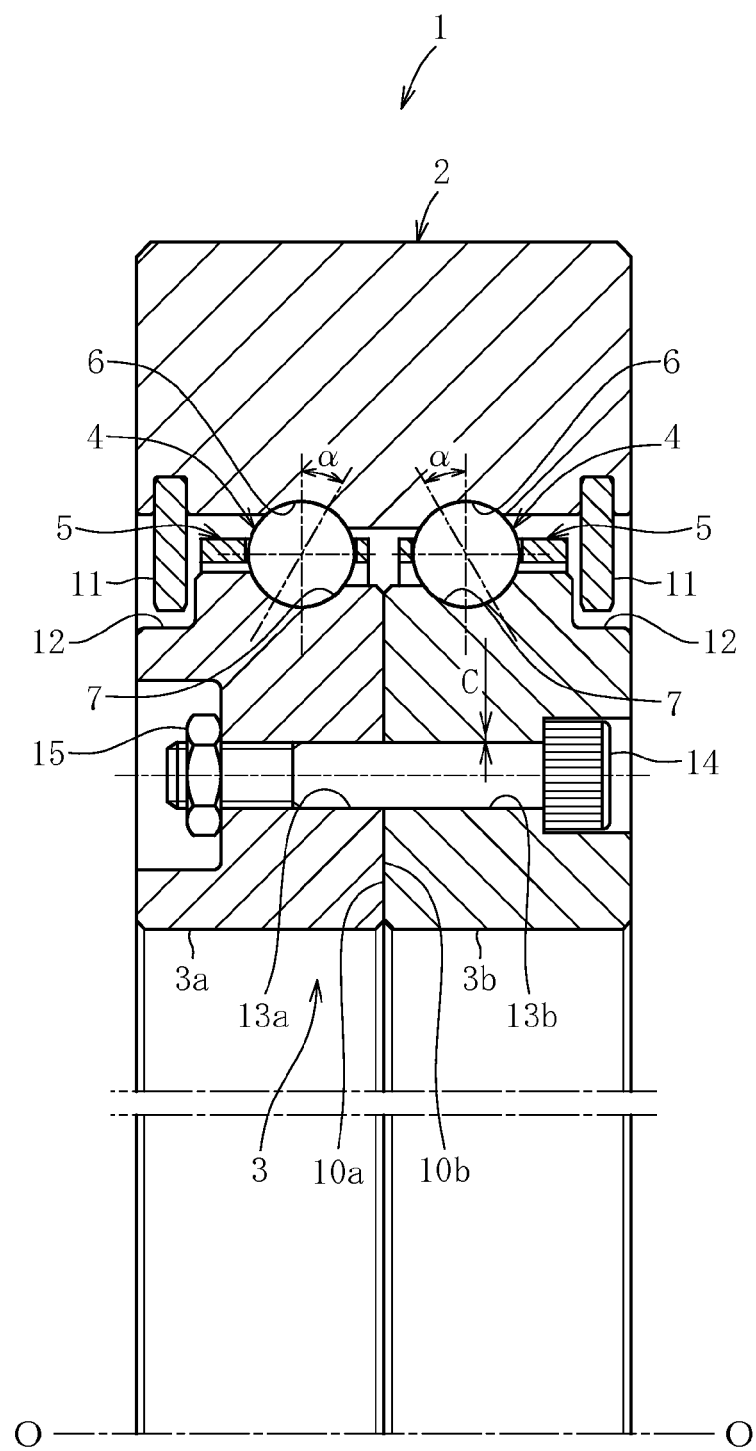
FIG. 2 is a vertical sectional view of the double-row rolling bearing according to the first embodiment at a different position in a circumferential direction.
Figure 3:
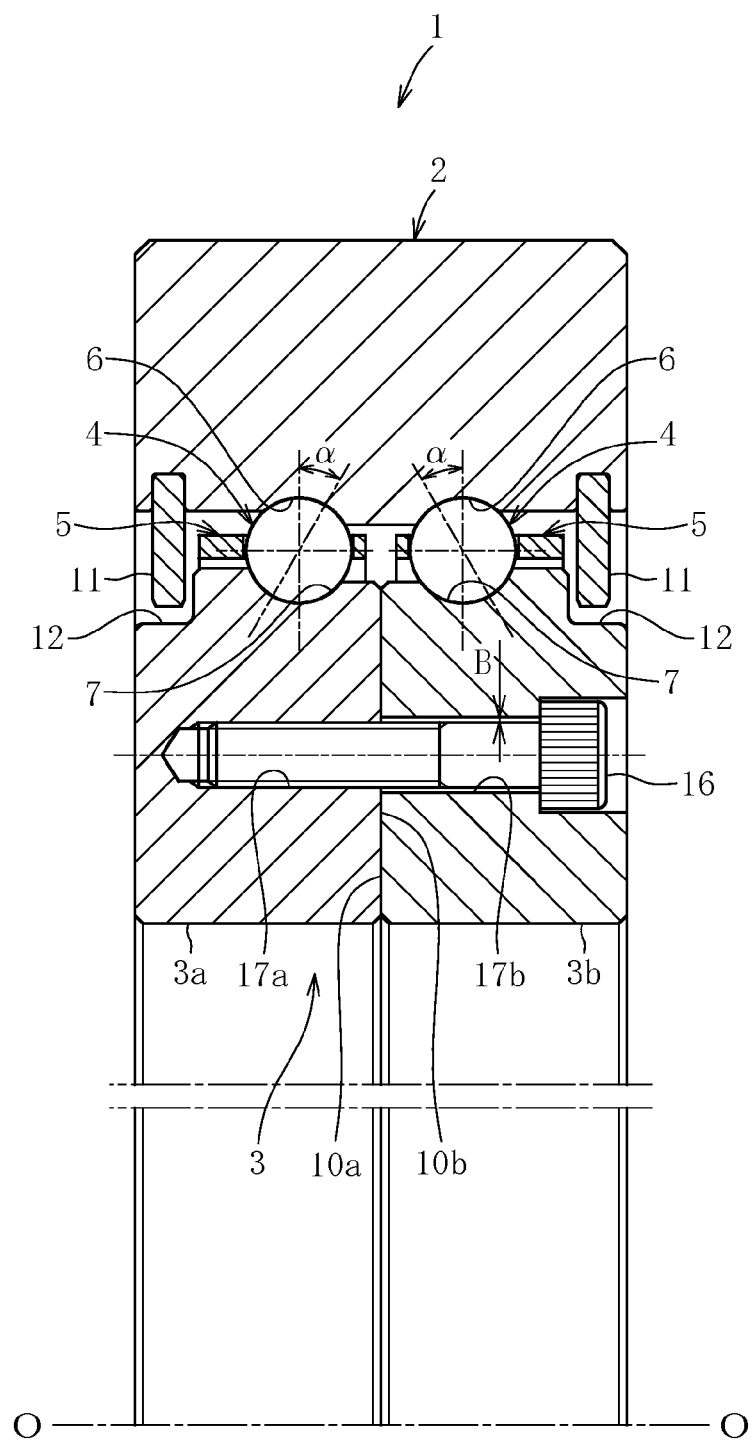
FIG. 3 is a vertical sectional view of the double-row rolling bearing according to the first embodiment at another different position in the circumferential direction.
Figure 4:
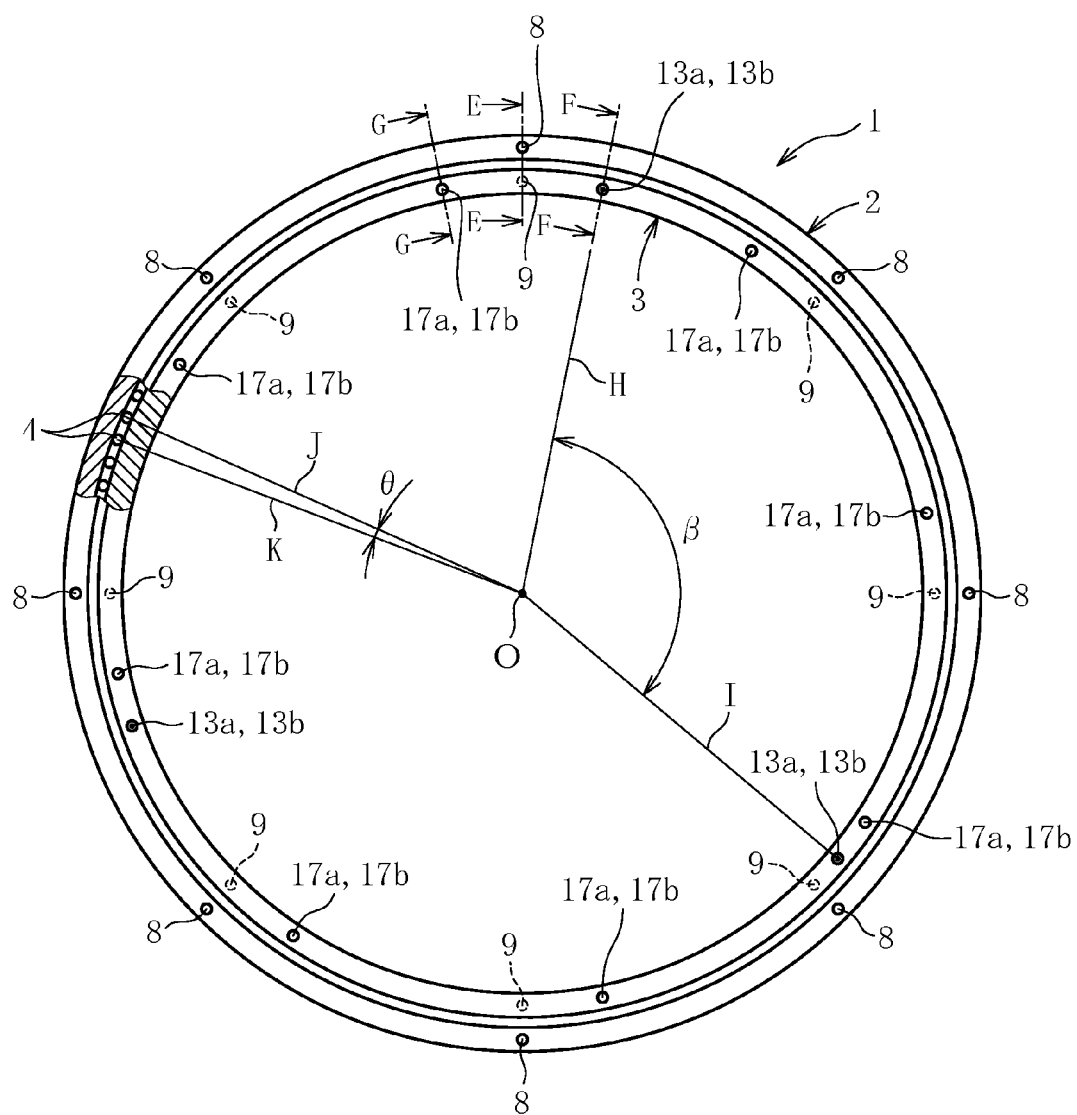
FIG. 4 is a front view of the double-row rolling bearing according to the first embodiment.

FIGS. 1 to 3 are vertical sectional views of the double-row rolling bearing according to this embodiment, and FIG. 4 is a front view partially including a transverse cross section. FIGS. 1 to 3 are vertical sectional views at different positions in a circumferential direction. FIG. 1 illustrates a vertical cross section taken along the line E-E of FIG. 4. FIG. 2 is a vertical cross section taken along the line F-F of FIG. 4. FIG. 3 is a vertical cross section taken along the line G-G of FIG. 4. As an overview of those vertical cross sections, in FIG. 4, a position of a mounting hole for mounting a double-row rolling bearing 1 on equipment for use is indicated by the E-E cross section, and the mounting hole is formed at eight positions in the circumferential direction. A position of a positioning hole for suppressing misalignment between a pair of raceway rings of an inner member 3 is indicated by the F-F cross section, and the positioning hole is formed at three positions in the circumferential direction. A position of a bolt fit-insertion hole for fastening the pair of raceway rings is indicated by the G-G cross section, and the bolt fit-insertion hole is formed at eight positions in the circumferential direction. The details are described later.

As illustrated in FIG. 1, the double-row rolling bearing 1 mainly comprises an outer member 2, the inner member 3, and balls 4 serving as rolling elements, and retainers 5. The outer member 2 and the inner member 3 both have a ring shape and are arranged concentrically. The inner member 3 is formed of a pair of raceway rings 3a and 3b, and end surfaces 10a and 10b abutting against each other of the raceway rings 3a and 3b have flat surfaces instead of a fitting structure. Two rows of raceway surfaces 6 and 6 are formed on an inner circumference of the outer member 2, and raceway surfaces 7 and 7 opposed to the raceway surfaces 6 and 6 of the outer member 2 are formed on each outer circumference of the pair of raceway rings 3a and 3b forming the inner member 3. Two rows of the balls 4 are assembled into a space between each of the raceway surfaces 6 and 6 of the outer member 2 and each of the raceway surfaces 7 and 7 of the inner member 3. The retainer 5 is arranged between the outer member 2 and the inner member 3, and the balls 4 in each row are retained at a predetermined interval in the circumferential direction.

The double-row rolling bearing 1 according to this embodiment is a double-row angular ball contact bearing having the balls 4 arranged in two rows. The bearing portions in both the rows are constructed in back-to-back arrangement, and an intersection of action lines of the loads of the rolling elements is formed on an outer side of a pitch circle of the balls 4. The balls 4 are held in contact with the raceway surfaces 6 and 7, respectively, at a contact angle $\alpha$, and the contact angle $\alpha$ is set to, for example, about 30°. The inner member 3 is formed of the pair of raceway rings 3a and 3b, and thus the double-row rolling bearing 1 is constructed in back-to-back arrangement, which is advantageous to a moment load. The end surfaces 10a and 10b of the pair of raceway rings 3a and 3b are brought into abutment against each other, thereby being capable of easily setting a bearing clearance (preload or minute clearance). The double-row rolling bearing 1 is an ultrathin double-row rolling bearing having a ratio Db/PCD of a diameter Db of each of the balls 4 to a pitch circle diameter PCD of the balls 4 of 0.03 or less.

A stepped portion 12 is formed on each of the raceway rings 3a and 3b by setting the outer circumference on the axially outer side of each of the raceway rings 3a and 3b to a small diameter. The stepped portion 12 forms a labyrinth in cooperation with a radially inner end portion of a seal member 11 mounted on the inner circumference of the outer member 2. Outer diameters of the respective stepped portions 12 are equal to each other, thereby allowing the use of the common seal member 11 on both sides.

A mounting hole 8 in the form of a through hole for allowing a bolt (not shown) to pass therethrough is formed in the outer member 2, and thus the outer member 2 is fastened to be fixed with the bolt to a mating member of the equipment for use. In this embodiment, as illustrated in FIG. 4, the mounting hole 8 is formed at eight positions with an equal interval in the circumferential direction. A screw hole 9 for allowing a bolt (not shown) to be screwed therein is formed in the raceway ring 3a of the inner member 3, and thus the inner member 3 is fastened to be fixed with the bolt to a mating member of the equipment for use. In the same way as in the outer member 2, as illustrated in FIG. 4, the screw hole 9 is formed at eight positions with an equal interval in the circumferential direction. However, the number of the positions of the mounting hole 8 and the screw hole 9 is not limited to eight, and needless to say, the mounting hole 8 and the screw hole 9 may be formed at any appropriate number of positions. Further, the mounting hole 8 and the screw hole 9 may be formed at an appropriate unequal interval instead of the equal interval.

In a normal use state in which a radially inner part and a radially outer part of the bearing are fitted to a shaft or a housing, the pair of raceway rings 3a and 3b forming the inner member 3 are fitted to the shaft, and thus the misalignment in a radial direction is regulated. However, as described above, in the double-row rolling bearing 1 according to this embodiment, the inner member 3 is fastened to be fixed with the bolt to the mating member of the equipment for use at a bearing end surface in a width direction. Therefore, the two rows of the raceway rings 3a and 3b are misaligned relatively in the radial direction, and this effect is significant, in particular, at a time of the action of a moment load. Thus, there is a concern about a problem such as a preload loss in this use state.

The double-row rolling bearing according to this embodiment is used in the above-mentioned state. The configuration for suppressing the misalignment between the pair of raceway rings 3a and 3b forming the inner member 3, which is a feature of the double-row rolling bearing, is described with reference to FIG. 2. As described above, the inner member 3 is formed of the pair of raceway rings 3a and 3b, and the end surfaces 10a and 10b abutting against each other of the raceway rings 3a and 3b have flat surfaces. In the raceway rings 3a and 3b, reamer holes 13a and 13b serving as positioning holes are formed in the form of a through hole for allowing a reamer bolt 14 serving as a positioning member to be fit-inserted therein. In this embodiment, as illustrated in FIG. 4, the reamer holes 13a and 13b are formed at three positions with an equal interval in the circumferential direction. However, the reamer holes 13a and 13b may be formed at an appropriate number of positions with an appropriate interval instead of being formed at three positions with an equal interval.

Specifically, as long as the number of fitting portions of the reamer holes 13a and 13b and the reamer bolt 14 is at least two, the positions in vertical and horizontal directions and in a rotation direction can be determined. However, a shear load is applied to the fitting portions, and hence it is desired to determine the number of the fitting portions in consideration of the shear load to be applied. In general, the shear stress of a bolt is from 60 to 70% of the tensile stress thereof, and hence the number of the reamer bolts 14 is determined by the following expression:

$$N \geq W/[\sigma \times (0.6 \sim 0.7) \times A]$$

where N represents the number of the reamer bolts 14, W represents a shear load to be applied, σ represents an allowable tensile stress of each of the reamer bolts 14, and A represents a cross-section area of each of the reamer bolts 14. Thus, in the double-row rolling bearing 1 according to this embodiment, the number of the fitting portions is set so as to satisfy the relationship of N≥W/[σ×(0.6~0.7)×A]. Accordingly, sufficient strength can be ensured with respect to the shear load.

The reamer bolt 14 comprises a radially outer portion finished with high accuracy and is capable of regulating a clearance between the reamer bolt 14 and the reamer holes 13a and 13b of the raceway rings 3a and 3b at a time of fitting. The fitting in this case is required to satisfy a relationship of clearance B>clearance C, where B represents a clearance between a radially outer part of a fixing bolt 16 (see FIG. 3) and a radially inner part of a fit-insertion hole 17b, and C represents a clearance between a radially outer part of the reamer bolt 14 and a radially inner part of the reamer holes 13a and 13b. It is ideal that the reamer bolt 14 and the reamer holes 13a and 13b be actually fitted (fitted in actual assembly operation), if possible.

Further, when the reamer bolt 14 is fit-inserted in the reamer holes 13a and 13b, the fitting of the reamer bolt 14 to the reamer holes 13a and 13b may become an interference fit. In this case, there is a risk in that strain corresponding to the number of the reamer bolts 14 may occur on the raceway surface 7. This strain may induce and increase a periodic vibration in association with the number of the rolling elements. Therefore, in order to prevent this, it is desired that each pitch angle between the reamer holes 13a and 13b and between the reamer holes 13b and 13b be set to an angle other than a multiple of the pitch angle between the rolling elements. In order to clearly illustrate the above-mentioned relationship, FIG. 4 being a front view of the double-row rolling bearing 1 partially includes a transverse cross section so as to illustrate an arrangement state of the rolling elements 4.

In this case, the pitch angle between the positioning holes refers to an angle β formed by two straight lines H and I, each connecting each center of the reamer holes 13a and 13a and the reamer holes 13b and 13b serving as the positioning holes, which are adjacent to each other in the circumferential direction, to an axial center O of the rolling bearing 1, as illustrated in FIG. 4. Further, the pitch angle between the rolling elements refers to an angle θ formed by two straight lines J and K, each connecting each center of the rolling elements 4 and 4, which are adjacent to each other in the circumferential direction, to the axial center O of the rolling bearing 1. That is, it is desired that the pitch angle β between the reamer holes serving as the positioning holes be set to an angle other than a multiple of the pitch angle θ between the rolling elements. The same applies to the pitch angles between the remaining reamer holes 13a and 13a and the reamer holes 13b and 13b. The same holds true both in Specification and Claims.

Specifically, the number of the balls 4 assembled in each row is 110 in the double-row rolling bearing 1 according to this embodiment, and hence the pitch angle θ between the rolling elements is 3.27°. In contrast, the reamer holes 13a and 13b are arranged at three positions with an equal interval in the circumferential direction, and hence the pitch angle β between the reamer holes is 120°. Thus, the pitch angle β between the positioning holes is set to an angle other than a multiple of the pitch angle θ between the rolling elements, and hence a periodic vibration in association with the number of the rolling elements can be prevented from being induced and increased.

The reamer holes 13a and 13b and the reamer bolt 14 are set as described above. The reamer bolt 14 is fit-inserted in the reamer holes 13a and 13b, and the pair of raceway rings 3a and 3b forming the inner member 3 are fastened to be fixed with a nut 15. With this, the misalignment in the radial direction between the raceway rings 3a and 3b can be suppressed. The reamer bolt 14 is preferred in terms of quality and cost because a commercially available bolt can be appropriately adopted as the reamer bolt 14.

Next, the pair of raceway rings 3a and 3b is fastened with the fixing bolt. This state is described with reference to FIG. 3. Of the pair of raceway rings 3a and 3b forming the inner member 3, a screw hole 17a is formed in the raceway ring 3a, and the bolt fit-insertion hole 17b is formed in the raceway ring 3b. As described above, the clearance B between the radially outer part of the fixing bolt 16 and the radially inner part of the fit-insertion hole 17b is set to be larger than the clearance C between the radially outer part of the reamer bolt 14 and the radially inner part of the reamer holes 13a and 13b.

As illustrated in FIG. 4, the screw hole 17a and the fit-insertion hole 17b are formed at eight positions with an equal interval in the circumferential direction. Note that, the screw hole 17a and the fit-insertion hole 17b may be formed at an appropriate number of positions with an appropriate interval instead of being formed at eight positions with an equal interval.

As illustrated in FIG. 3, the fixing bolt 16 is screwed in the screw hole 17a through the fit-insertion hole 17b until the end surfaces 10a and 10b of the raceway rings 3a and 3b abut against each other so as to fasten the raceway rings 3a and 3b. As described above, in the double-row rolling bearing 1 according to this embodiment, the reamer holes 13a and 13b are formed and the reamer bolt 14 is provided, thereby suppressing the misalignment between the pair of raceway rings 3a and 3b. Therefore, when the fixing bolt 16 is screwed in the screw hole 17 until the end surfaces 10a and 10b abut against each other as described above so as to fasten the raceway rings 3a and 3b, an appropriate preload (for example, about from −20 to 0 μm) caused by a constant position preload or a minute clearance (for example, about from 0 to 20 μm) is obtained uniformly in the two rows of right and left raceway rings 3a and 3b, thereby being capable of obtaining stable bearing performance. Further, the double-row rolling bearing 1 according to this embodiment does not have a fitting structure, and hence the double-row rolling bearing 1 can be easily manufactured at low cost.

Figure 5:
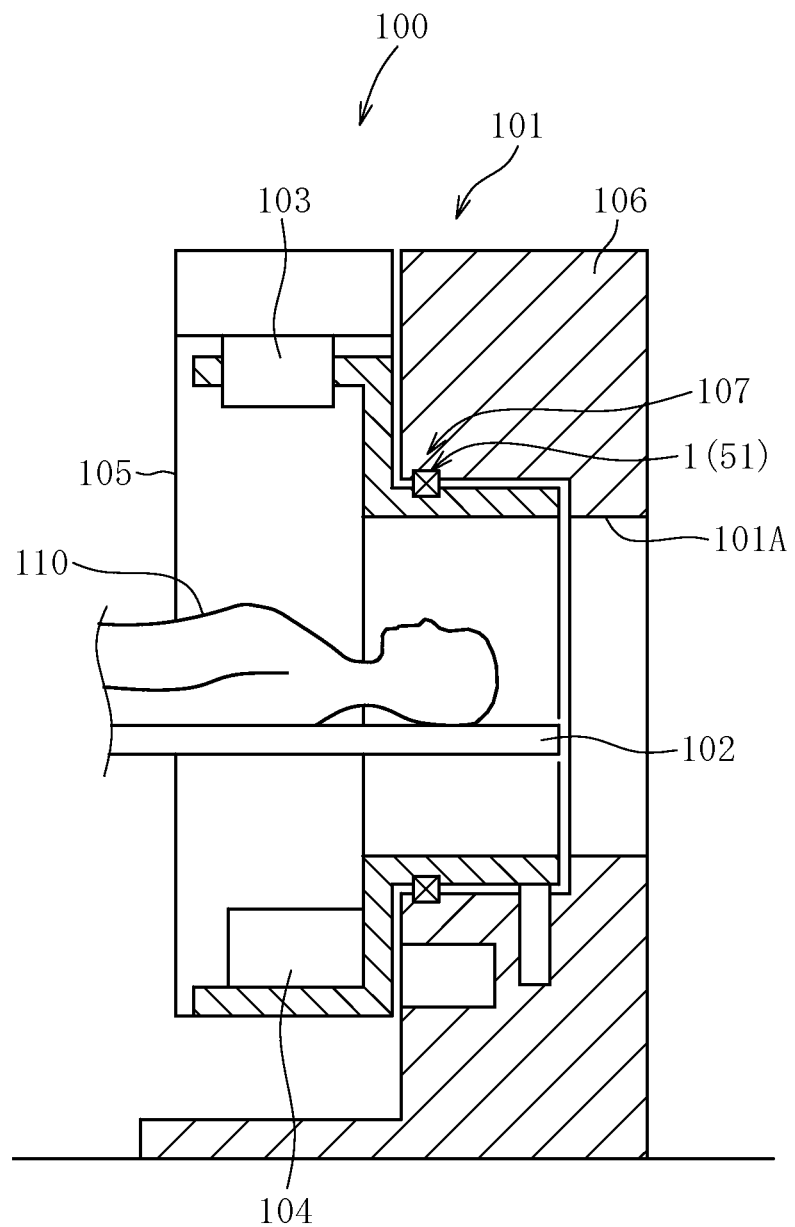
FIG. 5 is a schematic view illustrating a CT scanner.

FIG. 5 illustrates a state in which the double-row rolling bearing 1 according to this embodiment is used in a CT scanner 100. The double-row rolling bearing 1 is assembled into a space between a stationary unit 106 and a rotator 105 of the CT scanner 100. A bolt (not shown) is inserted in the mounting hole 8 of the outer member 2 illustrated in FIG. 1 so as to fasten and fix the outer member 2 to the stationary unit 106, and a bolt (not shown) is screwed in the screw hole 9 of the inner member 3 so as to fasten and fix the inner member 3 to the rotator 105. With this, the rotator 105 is rotatably supported by the stationary unit 106 through intermediation of the double-row rolling bearing 1. The rotator 105 has mounted thereon imaging devices such as an X-ray irradiation device 103 and a detection unit 104. Therefore, a large moment load is applied to the rolling bearing 1, and the rolling bearing 1 is used in such a load state at a high rotation speed of 120 rpm or more.

Although the double-row rolling bearing 1 according to this embodiment is used in the above-mentioned severe environment, the misalignment between the pair of raceway rings 3a and 3b is suppressed, and an appropriate preload or a minute clearance is uniformly obtained in the two rows of right and left raceway rings. As a result, the double-row rolling bearing 1 capable of achieving low noise, low vibration, high rigidity, high-speed rotation, and stable bearing performance can be obtained. Therefore, in the CT scanner 100, remarkable effects are obtained, such as alleviation of a burden on a patient by reduction in imaging time, decrease in an exposure dose due to imaging, and relief of anxiety and fear by low noise.

Figure 6:
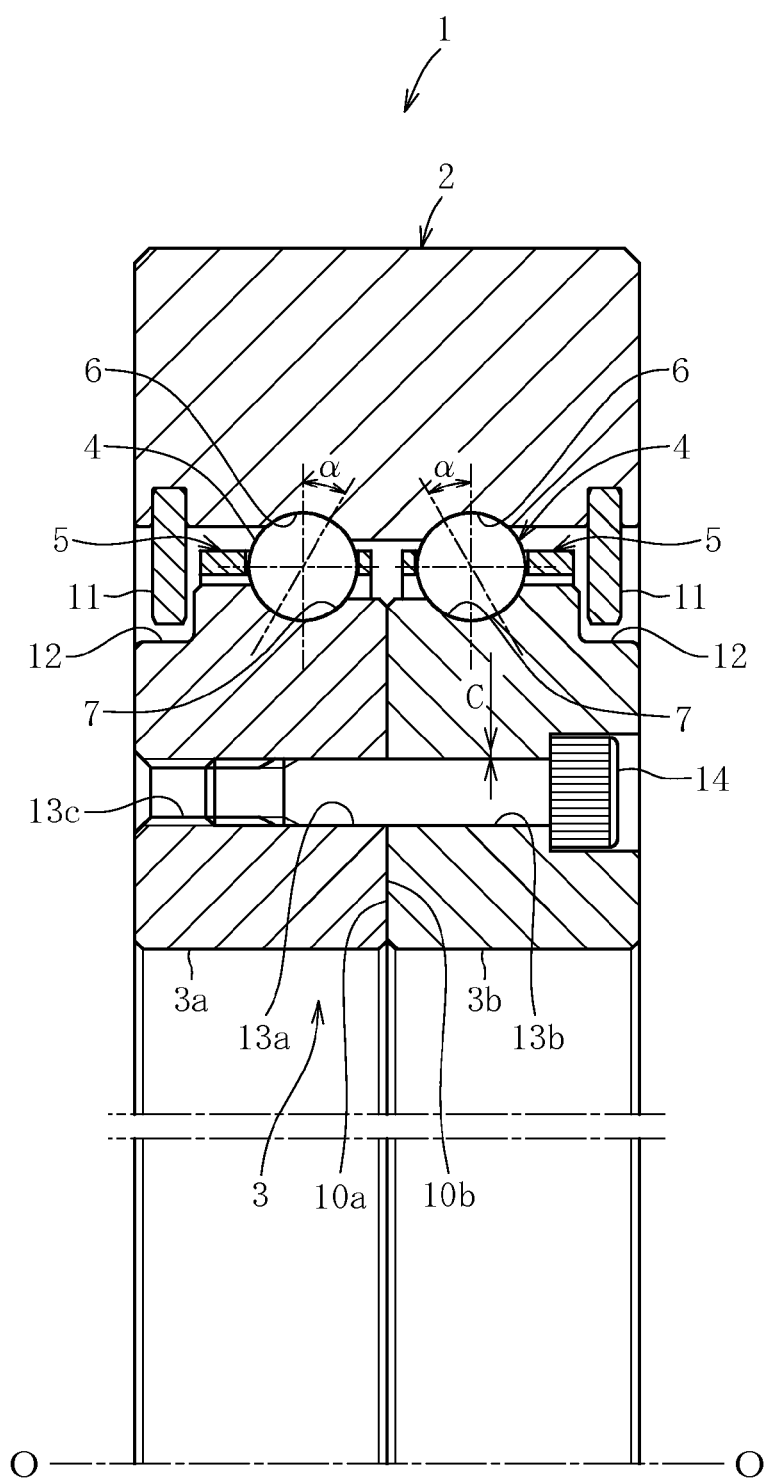
FIG. 6 is a vertical sectional view of a double-row rolling bearing according to a second embodiment of the present invention.

Next, a double-row rolling bearing according to a second embodiment of the present invention is described with reference to FIG. 6. The double-row rolling bearing 1 according to this embodiment is different from that of the first embodiment in a configuration of directly screwing the reamer bolt 14 in the raceway ring 3a, and the other configurations are the same as those of the first embodiment. Specifically, in this embodiment, FIG. 6 illustrates only a cross section having the reamer hole for suppressing the misalignment between the raceway rings of the inner member, and a cross section having the mounting hole for mounting the bearing on the equipment for use, a cross section having the fit-insertion hole for fastening both the right and left raceway rings, and a front of the bearing are the same as those of FIGS. 1, 3, and 4 according to the first embodiment. The parts having the same functions as those of the first embodiment are denoted by the same reference symbols, and main points are described.

In the double-row rolling bearing 1 according to this embodiment, the reamer hole 13a and a screw hole 13c are formed concentrically in the raceway ring 3a, and the same reamer hole 13b as that of the first embodiment is formed in the raceway ring 3b. The reamer bolt 14 is inserted in the reamer holes 13a and 13b and screwed in the screw hole 13c, to thereby fasten and fix the raceway rings 3a and 3b. With this, the misalignment between the pair of raceway rings 3a and 3b forming the inner member 3 is suppressed. In this embodiment, the nut for the reamer bolt 14 and counterboring therefor can be omitted, and hence the number of components and processing can be reduced. All of the details described in the above-mentioned first embodiment are applied to the other points, and the descriptions thereof are omitted.

Figure 7:
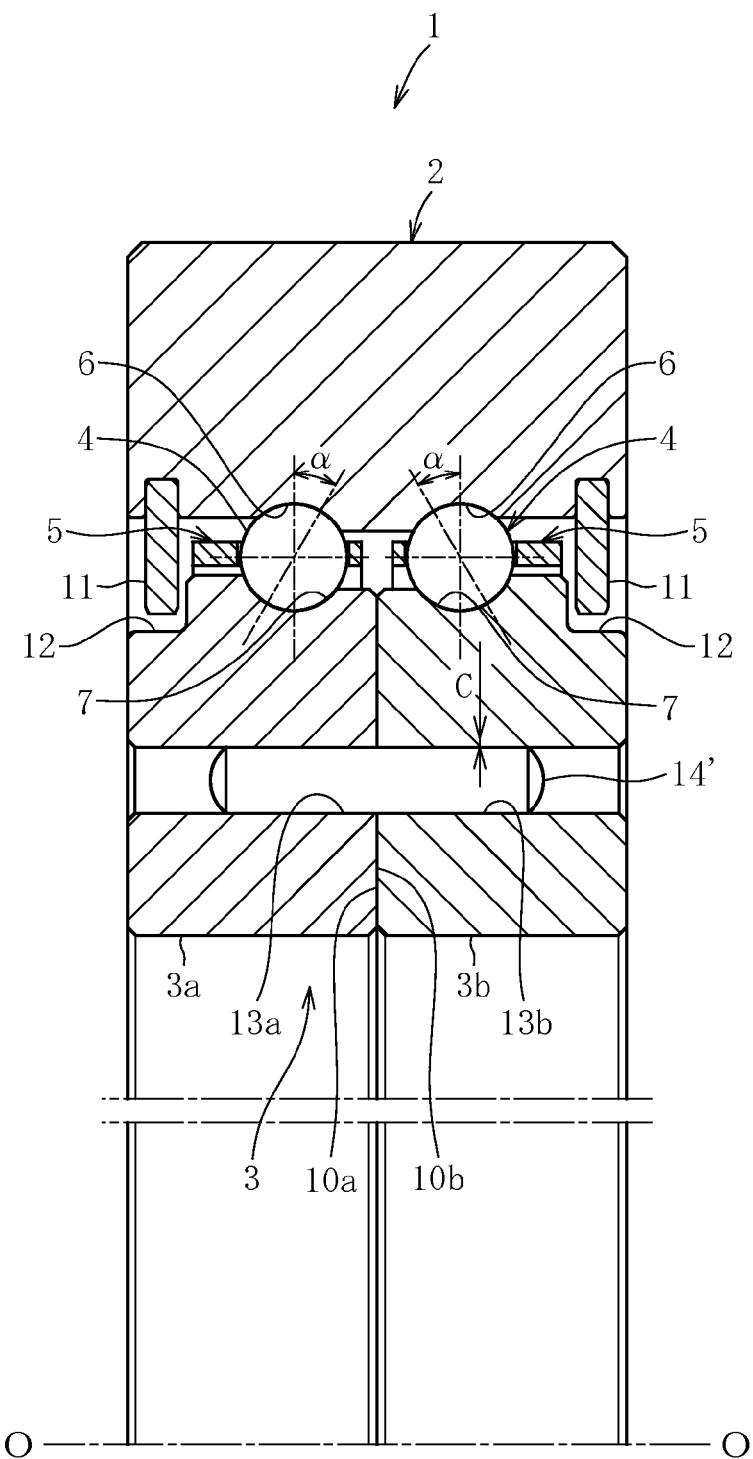
FIG. 7 is a vertical sectional view of a double-row rolling bearing according to a third embodiment of the present invention.

A double-row rolling bearing according to a third embodiment of the present invention is described with reference to FIG. 7. The double-row rolling bearing 1 according to this embodiment is different from that of the first embodiment in a configuration of using a positioning pin as the positioning member, and the other configurations are the same as those of the first embodiment. Also in this embodiment, FIG. 7 illustrates only a cross section having the reamer hole for suppressing the misalignment between the raceway rings of the inner member, and a cross section having the mounting hole for mounting the bearing on the equipment for use, a cross section having the fit-insertion hole for fastening both the right and left raceway rings, and a front of the bearing are the same as those of FIGS. 1, 3, and 4 according to the first embodiment. The parts having the same functions as those of the first embodiment are denoted by the same reference symbols, and main points are described.

In the double-row rolling bearing 1 according to this embodiment, a positioning pin 14' is fit-inserted in the reamer holes 13a and 13b of the raceway rings 3a and 3b, thereby suppressing the misalignment between the raceway rings 3a and 3b. As long as the fitting between the positioning pin 14' and the reamer holes 13a and 13b is an appropriate interference fit, fixing means for the poisoning pin is not required. In this embodiment, due to the use of the positioning pin 14', counterbored portions of the raceway rings 3a and 3b can be omitted, and further the positioning pin 14' is preferred in terms of quality and cost because a commercially available positioning pin can be appropriately adopted as the positioning pin 14'. All of the details descried in the first embodiment are applied to the other points with the reamer bolt of the above-mentioned first embodiment being interpreted as the positioning pin, and the descriptions thereof are omitted.

A double-row rolling bearing according to a fourth embodiment of the present invention is described with reference to FIG. 8. In the double-row rolling bearing in this embodiment, the reamer bolt is applied to the raceway rings having a fitting structure. Also in this embodiment, FIG. 8 illustrates only a cross section having the reamer hole for suppressing the misalignment between the raceway rings of the inner member, and main points of a configuration of forming the mounting hole for mounting the bearing on the equipment for use, a configuration of forming the fit-insertion hole for fastening both the right and left raceway rings, and a front of the bearing are the same as those of FIGS. 1, 3, and 4 according to the first embodiment.

Figure 8:
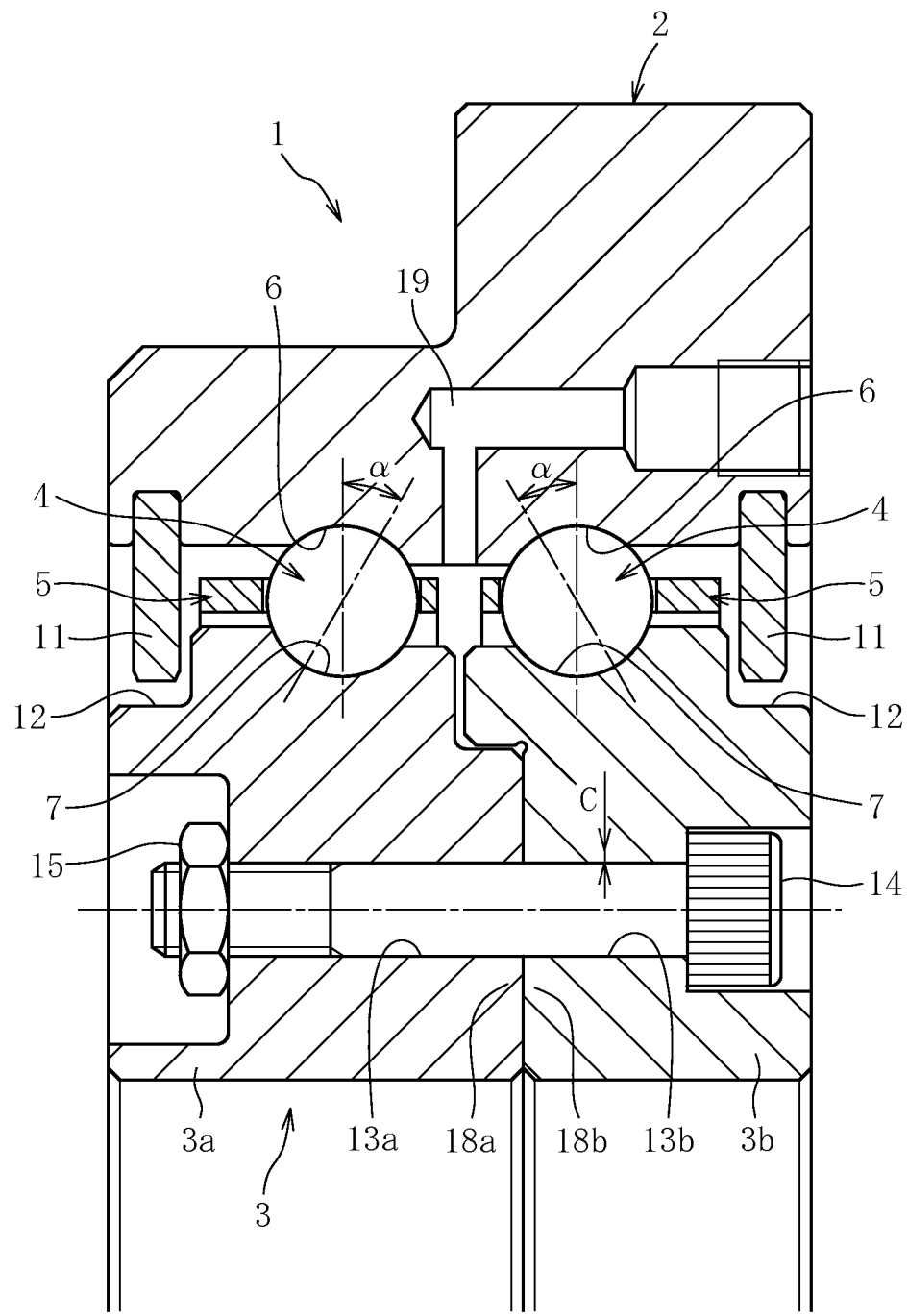
FIG. 8 is a vertical sectional view of a double-row rolling bearing according to a fourth embodiment of the present invention.
Figure 9:
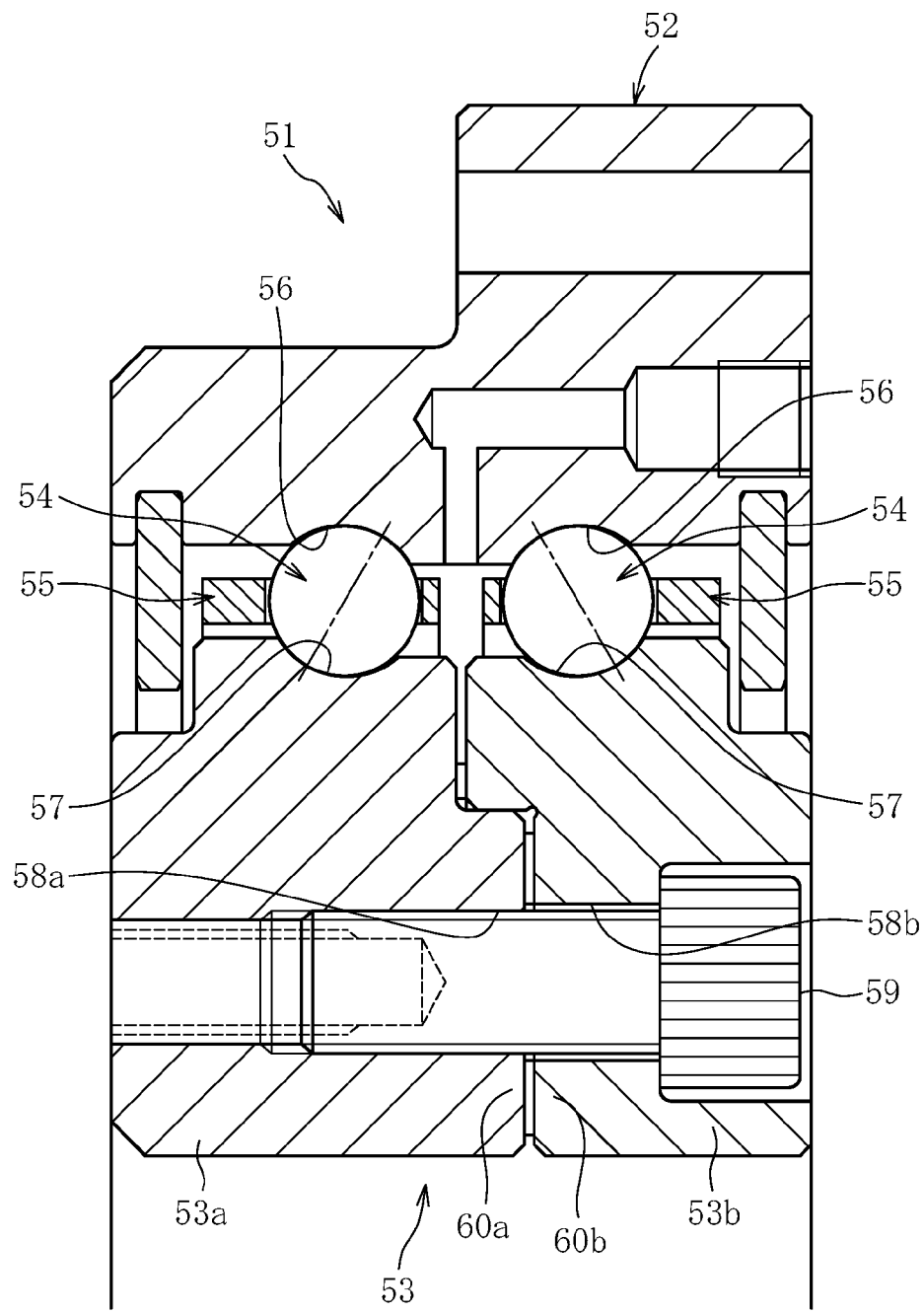
FIG. 9 is a vertical sectional view of a related-art double-row rolling bearing.

In this embodiment illustrated in FIG. 8, even in the case where the allowable dimension range of the fitting clearance is mitigated so as to suppress processing cost of a projection 18a and a recess 18b having a fitting structure of the raceway rings 3a and 3b, the misalignment between the raceway rings 3a and 3b can be suppressed with high accuracy by adding the reamer bolt 14 and the reamer holes 13a and 13b. As detailed different points from the first embodiment, the outer member 2 comprises a flange portion and also comprises a supply path 19 for a lubricant. The parts having the same functions as those of the first embodiment are denoted by the same reference symbols, and the descriptions thereof are omitted.

In summary, each of the embodiments described above is a double-row rolling bearing in which the misalignment in the radial direction between the pair of raceway rings is regulated by installing the positioning members (such as the reamer bolt and the positioning pin) for positioning the raceway rings in the radial direction besides the fixing bolt. The misalignment between the pair of raceway rings is thus suppressed. Therefore, when the fixing bolt is screwed in the raceway rings until the end surfaces of the raceway rings abut against each other so as to fasten the raceway rings, an appropriate preload or a minute clearance is uniformly obtained in the two rows of raceway rings. As a result, low noise, low vibration, high rigidity, and stable axial performance can be obtained even at high-speed rotation.

Each of the embodiments exemplifies the inner member 3 formed of the pair of raceway rings 3a and 3b. However, the present invention is not limited thereto, and the outer member 2 may be formed of a pair of raceway rings.

Each of the embodiments exemplifies the balls 4 as the rolling elements. However, the present invention is not limited thereto, and a conical roller or a cylindrical roller may be used.

The present invention is not limited to the above-mentioned embodiments. As a matter of course, the present invention may be carried out in various other embodiments without departing from the gist of the present invention. The scope of the present invention is defined by the claims, and encompasses meanings of equivalents of elements described in the claims and all modifications within the scope of the claims.

DESCRIPTION OF REFERENCE SIGNS 1 double-row rolling bearing
2 outer member
3 inner member
3a raceway ring
3b raceway ring
4 rolling element
5 retainer
6 raceway surface
7 raceway surface
8 mounting hole
9 screw hole
10a end surface
10b end surface
13a positioning hole
13b positioning hole
14 reamer bolt
14' positioning pin
16 fixing bolt
17a screw hole
17b fit-insertion hole
100 CT scanner
B clearance
C clearance
O axial center
α contact angle
β pitch angle between positioning holes
θ pitch angle between rolling elements

The invention claimed is:

1. A double-row rolling bearing, comprising:
an outer member having two raceway surfaces on an inner circumference thereof;
an inner member having two raceway surfaces on an outer circumference thereof, the inner member being arranged on an inner side of the outer member;
two rows of rolling elements, each of the rolling elements being located in a space between one of the two raceway surfaces of the outer member and one of the two raceway surfaces of the inner member; and
a retainer for retaining the rolling elements, wherein
any one of the outer member and the inner member comprises a pair of raceway rings, both of the raceway rings being fastened with a fixing bolt,
the pair of raceway rings have positioning holes into which a positioning member is fit-inserted, to thereby suppress misalignment in a radial direction of the pair of raceway rings, and
a fitting clearance between the positioning member and each of the positioning holes is set to be smaller than a fitting clearance between the fixing bolt and a fit-insertion hole for the fixing bolt.

2. The double-row rolling bearing according to claim 1, wherein the inner member comprises the pair of raceway rings.

3. The double-row rolling bearing according to claim 1, wherein the positioning member comprises a reamer bolt.

4. The double-row rolling bearing according to claim 3, wherein the following relationship is satisfied:

$$N \geq W/[\sigma \times (0.6 \sim 0.7) \times A]$$

where N represents a number of the reamer bolts, W represents a shear load to be applied, σ represents an allowable tensile stress of the reamer bolt, and A represents a cross-section area of the reamer bolt.

5. The double-row rolling bearing according to claim 1, wherein the positioning member comprises a positioning pin.

6. The double-row rolling bearing according to claim 1, wherein a number of the positioning holes is set to two or more.

7. The double-row rolling bearing according to claim 6, wherein a pitch angle between the positioning holes is set to an angle other than a multiple of a pitch angle between the rolling elements.

8. The double-row rolling bearing according to claim 1, wherein the double-row rolling bearing comprises a double-row angular contact ball bearing.

9. A CT scanner comprising the double-row rolling bearing according to claim 1.

10. The double-row rolling bearing according to claim 1, wherein end surfaces abutting against each other of the pair of raceway rings have flat surfaces.

11. The double-row rolling bearing according to claim 10, wherein the inner member comprises the pair of raceway rings.

12. The double-row rolling bearing according to claim 10, wherein the positioning member comprises a reamer bolt.

13. The double-row rolling bearing according to claim 10, wherein the positioning member comprises a positioning pin.

14. The double-row rolling bearing according to claim 10, wherein a number of the positioning holes is set to two or more.

15. The double-row rolling bearing according to claim 10, wherein the double-row rolling bearing comprises a double-row angular contact ball bearing.

16. A CT scanner comprising the double-row rolling bearing according to claim 10.

* * * * *